US009402767B2

(12) United States Patent
Schieber et al.

(10) Patent No.: US 9,402,767 B2
(45) Date of Patent: Aug. 2, 2016

(54) OCULAR IMPLANT ARCHITECTURES

(71) Applicant: Ivantis, Inc., Irvine, CA (US)

(72) Inventors: Andrew T. Schieber, Irvine, CA (US); Charles L. Euteneuer, St. Michael, MN (US)

(73) Assignee: IVANTIS, INC., Irvine, CA (US)

( * ) Notice: Subject to any disclaimer, the term of this patent is extended or adjusted under 35 U.S.C. 154(b) by 238 days.

(21) Appl. No.: 13/763,394

(22) Filed: Feb. 8, 2013

(65) Prior Publication Data
US 2013/0150959 A1    Jun. 13, 2013

Related U.S. Application Data

(63) Continuation of application No. 13/366,073, filed on Feb. 3, 2012, now Pat. No. 8,372,026, which is a continuation of application No. 12/236,254, filed on Sep. 23, 2008, now abandoned, which is a continuation-in-part of application No. 11/860,318, filed on Sep. 24, 2007, now Pat. No. 7,740,604.

(60) Provisional application No. 61/033,746, filed on Mar. 4, 2008.

(51) Int. Cl.
*A61F 9/007* (2006.01)
*A61F 2/14* (2006.01)

(52) U.S. Cl.
CPC .............. *A61F 9/00781* (2013.01); *A61F 2/14* (2013.01)

(58) Field of Classification Search
CPC .............. A61F 9/00781; A61F 9/0008; A61F 9/00868; A61F 9/00891; A61M 2210/0612
USPC .................. 604/8, 9, 289, 294; 623/5.11–5.13
See application file for complete search history.

(56) References Cited

U.S. PATENT DOCUMENTS

| 703,296 A | 6/1902 | Arnold |
| 1,601,709 A | 10/1926 | Windom |
| 2,716,983 A | 9/1955 | George et al. |
| 3,071,135 A | 1/1963 | Baldwin et al. |
| 3,788,327 A | 1/1974 | Donowitz et al. |
| 3,811,442 A | 5/1974 | Maroth |

(Continued)

FOREIGN PATENT DOCUMENTS

| AU | 1998/76197 B2 | 2/1999 |
| CN | 1950091 A | 4/2007 |

(Continued)

OTHER PUBLICATIONS

Wardle et al.; U.S. Appl. No. 14/139,403 entitled "Ocular implants for delivery into the eye," filed Dec. 23, 2013.

(Continued)

*Primary Examiner* — Howie Matthews
(74) *Attorney, Agent, or Firm* — Shay Glenn LLP

(57) ABSTRACT

An ocular implant having a first spine; a second spine; a first strut extending in an axial direction Z between the first spine and the second spine; a second strut extending in an axial direction Z between the first spine and the second spine; wherein an angular dimension θ of a first edge of each strut undulates as the strut extends in the axial direction Z between the first spine and the second spine; and wherein a radius r of an outer surface of each strut remains substantially constant as the strut extends the axial direction Z between the first spine and the second spine.

19 Claims, 11 Drawing Sheets

(56) References Cited

U.S. PATENT DOCUMENTS

| | | |
|---|---|---|
| 3,948,271 A | 4/1976 | Akiyama |
| 4,037,604 A | 7/1977 | Newkirk |
| 4,428,746 A | 1/1984 | Mendez |
| 4,457,757 A | 7/1984 | Molteno |
| 4,601,713 A | 7/1986 | Fuquo |
| 4,689,040 A | 8/1987 | Thompson |
| 4,699,140 A | 10/1987 | Holmes et al. |
| 4,706,669 A | 11/1987 | Schlegel |
| 4,722,724 A | 2/1988 | Schocket |
| 4,733,665 A | 3/1988 | Palmaz |
| 4,750,901 A | 6/1988 | Molteno |
| 4,826,478 A | 5/1989 | Schocket |
| 4,861,341 A | 8/1989 | Woodburn |
| 4,880,000 A | 11/1989 | Holmes et al. |
| 4,886,488 A | 12/1989 | White |
| 4,919,130 A | 4/1990 | Stoy et al. |
| 4,934,363 A | 6/1990 | Smith et al. |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 5,092,837 A | 3/1992 | Ritch et al. |
| 5,127,901 A | 7/1992 | Odrich |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,246,452 A | 9/1993 | Sinnott |
| 5,290,267 A | 3/1994 | Zimmermann |
| 5,360,399 A | 11/1994 | Stegmann |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,536,259 A | 7/1996 | Utterberg |
| 5,575,780 A | 11/1996 | Saito |
| 5,591,223 A | 1/1997 | Lock et al. |
| 5,613,972 A | 3/1997 | Lee et al. |
| 5,626,558 A | 5/1997 | Suson |
| 5,653,753 A | 8/1997 | Brady et al. |
| 5,676,669 A | 10/1997 | Colvard |
| 5,792,099 A | 8/1998 | DeCamp et al. |
| 5,807,302 A | 9/1998 | Wandel |
| 5,865,831 A | 2/1999 | Cozean et al. |
| 5,868,697 A | 2/1999 | Richter et al. |
| 5,879,319 A | 3/1999 | Pynson et al. |
| 5,893,837 A | 4/1999 | Eagles et al. |
| 5,919,171 A | 7/1999 | Kira et al. |
| 5,948,427 A | 9/1999 | Yamamoto et al. |
| 5,968,058 A | 10/1999 | Richter et al. |
| 6,007,511 A | 12/1999 | Prywes |
| 6,050,970 A | 4/2000 | Baerveldt |
| 6,102,045 A | 8/2000 | Nordquist et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 | 6/2001 | Cozean et al. |
| D444,874 S | 7/2001 | Haffner et al. |
| 6,328,747 B1 | 12/2001 | Nun |
| 6,375,642 B1 | 4/2002 | Grieshaber et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,094,225 B2 | 8/2006 | Tu et al. |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,034,105 B2 | 10/2011 | Stegmann et al. |
| 8,123,729 B2 | 2/2012 | Yamamoto et al. |
| 8,267,882 B2 | 9/2012 | Euteneuer et al. |
| 8,282,592 B2 | 10/2012 | Schieber et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,945,038 B2 | 2/2015 | Yablonski |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0052653 A1 | 5/2002 | Durgin |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0193805 A1 | 12/2002 | Ott et al. |
| 2003/0004457 A1 | 1/2003 | Andersson |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0082939 A1 | 4/2004 | Berlin |
| 2004/0088048 A1 | 5/2004 | Richter et al. |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0122380 A1 | 6/2004 | Utterberg |

(56) References Cited

U.S. PATENT DOCUMENTS

| | | |
|---|---|---|
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0244464 A1 | 11/2005 | Hughes |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0241749 A1 | 10/2006 | Tu et al. |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0135681 A1 | 6/2007 | Chin et al. |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0219509 A1 | 9/2007 | Tashiro et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0228127 A1 | 9/2008 | Burns et al. |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082860 A1 | 3/2009 | Schieber et al. |
| 2009/0082862 A1 | 3/2009 | Schieber et al. |
| 2009/0104248 A1 | 4/2009 | Rapacki et al. |
| 2009/0132040 A1 | 5/2009 | Frion et al. |
| 2009/0138081 A1 | 5/2009 | Bergheim et al. |
| 2009/0182421 A1 | 7/2009 | Silvestrini et al. |
| 2009/0198248 A1 | 8/2009 | Yeung et al. |
| 2009/0204053 A1 | 8/2009 | Nissan et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2010/0004580 A1 | 1/2010 | Lynch et al. |
| 2010/0057072 A1 | 3/2010 | Roman et al. |
| 2010/0114309 A1 | 5/2010 | de Juan et al. |
| 2010/0137981 A1 | 6/2010 | Silvestrini et al. |
| 2010/0173866 A1 | 7/2010 | Hee et al. |
| 2010/0234726 A1 | 9/2010 | Sirimanne et al. |
| 2010/0234790 A1 | 9/2010 | Tu et al. |
| 2011/0009874 A1 | 1/2011 | Wardle et al. |
| 2011/0098809 A1 | 4/2011 | Wardle et al. |
| 2011/0319806 A1 | 12/2011 | Wardle |
| 2012/0010702 A1 | 1/2012 | Stegmann et al. |
| 2012/0323159 A1 | 12/2012 | Wardle et al. |
| 2013/0006165 A1 | 1/2013 | Euteneuer et al. |
| 2013/0079701 A1 | 3/2013 | Schieber et al. |
| 2013/0231603 A1 | 9/2013 | Wardle et al. |
| 2013/0331761 A1 | 12/2013 | Euteneuer et al. |
| 2013/0338563 A1 | 12/2013 | Schieber et al. |
| 2014/0066821 A1 | 3/2014 | Friedland et al. |
| 2014/0249463 A1 | 9/2014 | Wardle et al. |
| 2014/0323944 A1 | 10/2014 | Schieber et al. |

FOREIGN PATENT DOCUMENTS

| | | |
|---|---|---|
| DE | 4226476 C1 | 8/1993 |
| DE | 19840047 A1 | 3/2000 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| JP | H10-504978 A | 5/1998 |
| JP | 11123205 | 5/1999 |
| JP | 2002541976 | 12/2002 |
| JP | 2002541977 | 12/2002 |
| JP | 2002542872 | 12/2002 |
| JP | 2006517848 | 8/2006 |
| JP | 2006289075 A | 10/2006 |

(56) References Cited

FOREIGN PATENT DOCUMENTS

| | | |
|---|---|---|
| JP | 2010509003 | 3/2010 |
| JP | 2011502649 | 1/2011 |
| WO | WO 00/07525 A1 | 2/2000 |
| WO | WO 00/64389 A1 | 11/2000 |
| WO | WO 00/64393 A1 | 11/2000 |
| WO | WO 01/97727 A1 | 12/2001 |
| WO | WO 02/36052 A1 | 5/2002 |
| WO | WO 02/074052 A2 | 9/2002 |
| WO | WO 02/080811 A2 | 10/2002 |
| WO | WO 03/015659 A2 | 2/2003 |
| WO | WO 03/045290 A1 | 6/2003 |
| WO | WO 2004/054643 A1 | 7/2004 |
| WO | WO 2004/093761 A1 | 11/2004 |
| WO | WO 2005/105197 A2 | 11/2005 |
| WO | WO 2006/066103 A2 | 6/2006 |
| WO | WO 2007/035356 A2 | 3/2007 |
| WO | WO 2007/047744 A2 | 4/2007 |
| WO | WO 2007/087061 A2 | 8/2007 |
| WO | WO 2008/002377 A1 | 1/2008 |
| WO | WO 2008/005873 A2 | 1/2008 |
| WO | WO 2009/120960 A2 | 10/2009 |

OTHER PUBLICATIONS

Wardle et al.; U.S. Appl. No. 14/146,587 entitled "Delivering Ocular Implants Into the Eye," filed Jan. 2, 2014.

Schieber et al.; U.S. Appl. No. 14/246,363 entitled "Ocular implants with asymmetric flexibility," filed Apr. 7, 2014.

Bahler, et al.; Trabecular bypass stents decrease intraocular pressure in cultured human anterior segments; Amer. Journal of Ophthalmology; vol. 138, No. 6; pp. 988-994.e2; Dec. 2004.

D'Ermo, et al.; Our results with the operation of ab externo trabeculotomy; Ophthalmologica; vol. 163; pp. 347-355; Feb. 1971.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Johnstone et al.; "Microsurgery of Schlemm's Canal and the Human Aqueous Outflow System;" American Journal of Ophthalmology, vol. 76 (6): 906-917; Dec. 1973.

Lee et al.; Aqueous-venous shunt and intraocular pressure. Preliminary report of animal studies; Investigative Ophthalmology; vol. 5; No. 1; pp. 59-64; Feb. 1966.

Moses, Robert; The effect of intraocular pressure on resistance to outflow; Survey of Ophthalmology; vol. 22; No. 2; pp. 88-100; Sep.-Oct. 1977.

Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.

Rosenquist et al.; Outflow resistance of enucleated human eyes at two different perfusion pressures and different extents of trabeculotomy; Current Eye Res.; vol. 8; No. 12; pp. 1233-1240; Dec. 1989.

Savage, James; Gonioscopy in the management of glaucoma; Am. Academy of Ophthalmology; Focal Points; vol. XXIV; No. 3; pp. 1-14; Mar. 2006.

Schultz, Jared; Canaloplasty procedure shows promise for open-angle glaucoma in European study; Ocular Surgery News; vol. 34; Mar. 1, 2007.

Smit et al.; Effects of viscoelastic injection into schlemm's canal in primate and human eyes; J. Am. Academy of Ophthalmology; vol. 109; No. 4; pp. 786-792; Apr. 2002.

Spiegel et al.; Schlemm's canal implant: a new method to lower intraocular pressure in patients with POAG?; Ophthalmic Surgery and Lasers; vol. 30; No. 6; pp. 492-494; Jun. 1999.

Lynch, Mary G.; U.S. Appl. No. 60/131,030 entitled "Devices and methods for treating glaucoma by enhancing aqueous outflow through schlemm's canal and anterior chamber angle ," filed Apr. 26, 1999.

Wardle et al.; U.S. Appl. No. 13/330,592 entitled "Delivering Ocular Implants Into the Eye," filed Dec. 19, 2011.

Schieber et al.; U.S. Appl. No. 13/776,592 entitled "Glaucoma Treatment Method," filed Feb. 25, 2013.

Wardle et al.; U.S. Appl. No. 13/744,351 entitled "Suspended goniolens system," filed Jan. 17, 2013.

Wardle et al.; U.S. Appl. No. 13/793,638 entitled "Ocular Implants for Delivery into an Anterior Chamber of the Eye," filed Mar. 11, 2013.

Wardle et al.; U.S. Appl. No. 14/363,409 entitled "Delivering ocular implants into the eye," filed Jun. 6, 2014.

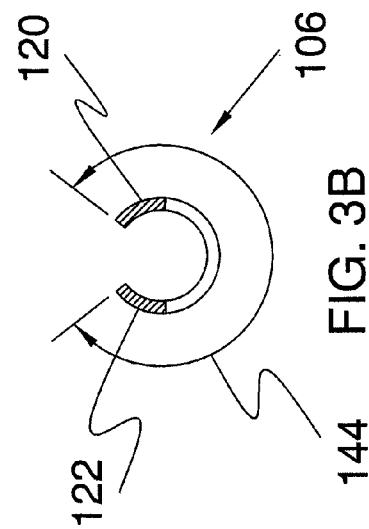
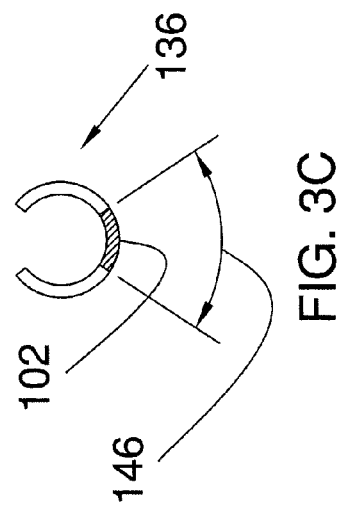
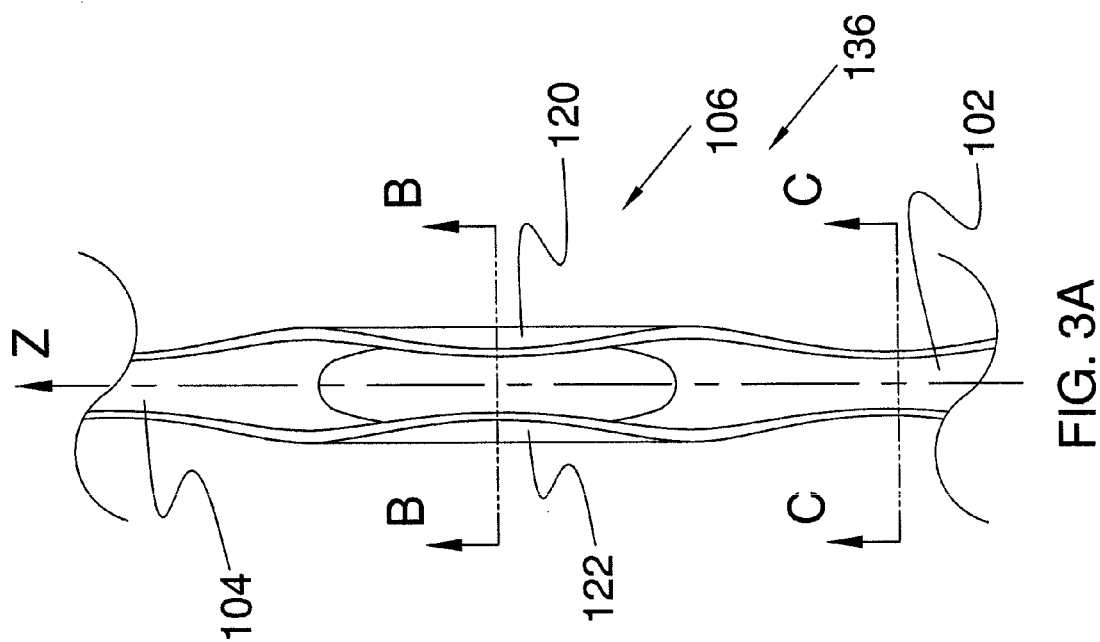

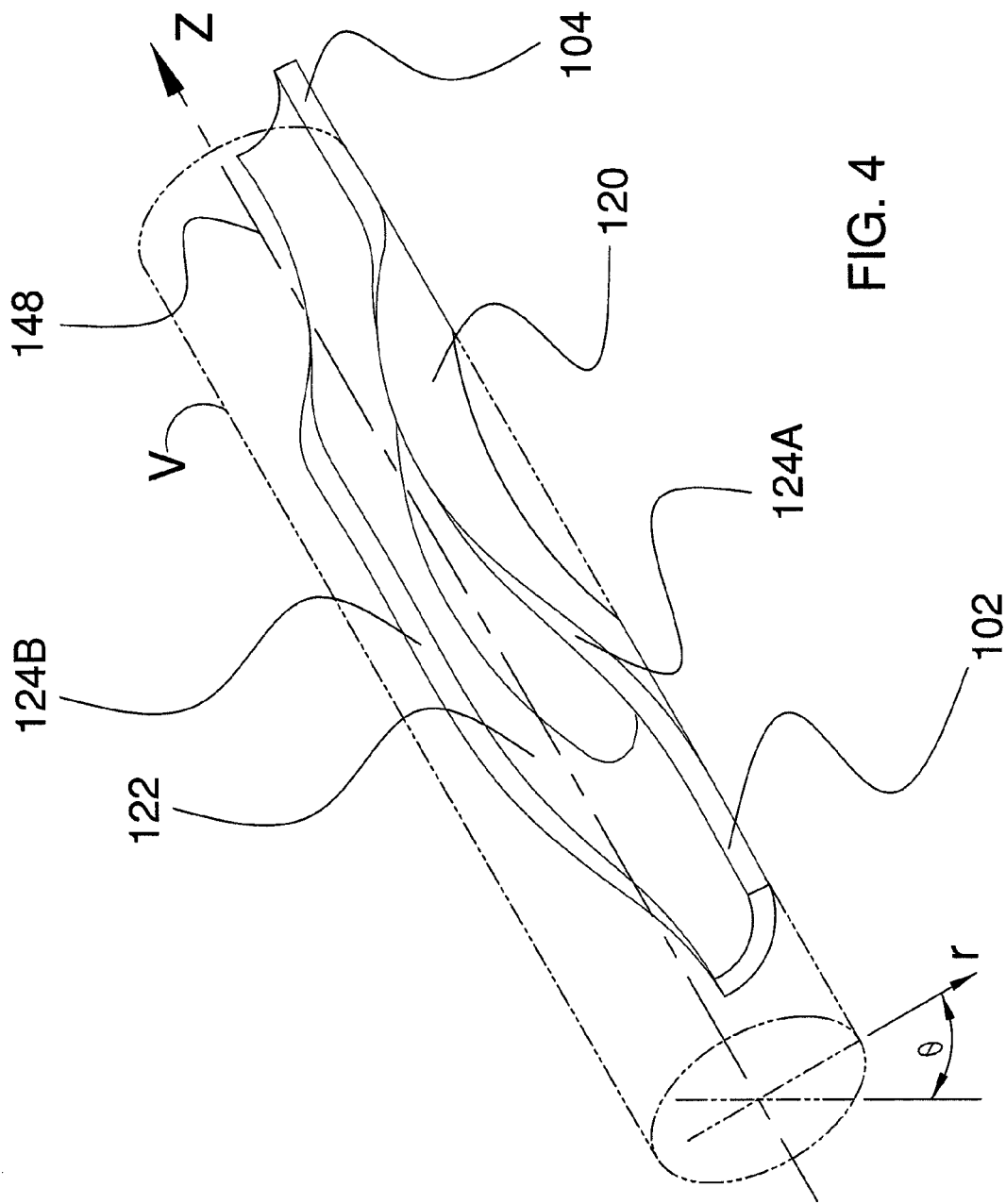

SECTION H-H

SECTION G-G

SECTION F-F

SECTION E-E

SECTION D-D

| | z [MICROMETERS] | r [MICROMETERS] | θ [DEGREES] |
|---|---|---|---|
| SECTION D-D | 622 | 145 | 82 |
| SECTION E-E | 780 | 145 | 112 |
| SECTION F-F | 1054 | 145 | 142 |
| SECTION G-G | 1328 | 145 | 112 |
| SECTION H-H | 622 | 145 | 82 |

FIG. 7

OCULAR IMPLANT ARCHITECTURES

CROSS REFERENCE TO RELATED APPLICATIONS

This application is a continuation of U.S. application Ser. No. 13/366,073, filed Feb. 3, 2012, now U.S. Pat. No. 8,372,026; which is a continuation of U.S. application Ser. No. 12/236,254, filed Sep. 23, 2008, now abandoned; which claims priority to U.S. Provisional Application No. 61/033,746, filed Mar. 4, 2008. U.S. application Ser. No. 12/236,254 is also a continuation-in-part of U.S. application Ser. No. 11/860,318, filed Sep. 24, 2007, now U.S. Pat. No. 7,740,604. The disclosures of the preceding patents and patent applications are incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to devices that are implanted within the eye. More particularly, the present invention relates to devices that facilitate the transfer of fluid from within one area of the eye to another area of the eye.

BACKGROUND OF THE INVENTION

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Ophthalmology (February 1966)). Other early glaucoma treatment implants led from the anterior chamber to a subconjunctival bleb (e.g., U.S. Pat. No. 4,968,296 and U.S. Pat. No. 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. No. 6,450,984; U.S. Pat. No. 6,450,984).

SUMMARY OF THE INVENTION

One aspect of the invention provides an ocular implant having a first spine; a second spine; a first strut extending in an axial direction Z between the first spine and the second spine; a second strut extending in an axial direction Z between the first spine and the second spine; wherein an angular dimension θ of a first edge of each strut undulates as the strut extends in the axial direction Z between the first spine and the second spine; and wherein a radius r of an outer surface of each strut remains substantially constant as the strut extends the axial direction Z between the first spine and the second spine.

Yet another aspect of the invention provides an ocular implant having a first spine section; a second spine section; and a first frame extending between the first spine section and the second spine section, the frame having a diameter of between 0.005 inches and 0.04 inches, the ocular implant being adapted to be disposed within a canal of Schlemm in a human eye.

In some embodiments, the first spine section, the second spine section, and the first frame form portions of a single tubular wall. Each spine section may optionally have only a single spine. In some embodiments, each spine section has an arcuate shape in lateral cross section. In some embodiments, the first spine has a first circumferential extent and the first frame has a second circumferential extent, wherein the second circumferential extent is greater than the first circumferential extent.

In some embodiments, the first frame has a first strut and a second strut and may have only two struts. Each strut may optionally have an arcuate shape in lateral cross section.

In embodiments in which the first strut has a first edge (partially defining, e.g., a first opening in the ocular implant), an angular dimension θ of the first edge may undulate as the strut extends in an axial direction Z between the first spine and the second spine. An angular dimension θ of the first edge may also first increase, then decrease, as the strut extends in an axial direction Z between the first spine and the second spine. Also, a radius r of the first edge may remain substantially constant as the strut extends in axial dimension Z between the first spine and the second spine.

In some embodiments, the first strut has a thickness that is substantially constant in a radial direction. In some embodiments, the first strut has a width extending in an arc along a circumferential direction. In some embodiments, the first strut has a length extending in an axial direction that is generally parallel to a longitudinal axis of the ocular implant.

The first spine section and the second spine section may be axially aligned with one another. A shape of the second strut may also be a mirror image of a shape of the first strut.

Some embodiments of the ocular implant have a second frame extending between the second spine and a third spine. Some embodiments of the ocular implant have a first opening extending between the first edge of the first strut and the first edge of the second strut. In some embodiments, a second edge of the first strut and a second edge of the second strut defining a second opening. In some embodiments, the first strut, the second strut, the first spine section, and the second spine section all define a cylindrical volume.

Some embodiments of the ocular implant have a therapeutic agent (e.g., an anti-glaucoma drug such as a prostaglandin analog like latanprost) deposited on the frame and spine sections.

Still another aspect of the invention provides an ocular implant having a first spine; a second spine; a first frame comprising a first strut and a second strut; each strut extending in an axial direction Z between the first spine and the second spine; a first opening of the ocular implant extending between a first edge of the first strut and a first edge of the second strut; a second edge of the first strut and a second edge of the second strut defining a second opening; wherein an angular dimension θ of the first edge of each strut undulates as the strut extends in the axial direction Z between the first spine and the second spine; and wherein a radius r of an outer surface of each strut remains substantially constant as the strut extends the axial direction Z between the first spine and the second spine.

BRIEF DESCRIPTION OF THE DRAWINGS

FIG. 3A is a plan view showing a portion of the ocular implant shown in the previous figure. The ocular implant includes a first frame comprising a first strut and a second strut. In the exemplary embodiment of FIG. 3A, each strut undulates in a circumferential direction while, at the same time, extending in the axial direction Z between a first spine and a second spine.

FIG. 3B is a lateral cross-sectional view of the ocular implant shown in the previous figure. Section line B-B intersects the first strut and second strut of the ocular implant at the point where the circumferential undulation of these struts is at it's maximum. These struts form a frame having circumferential extent that is illustrated using dimension lines in FIG. 3B.

FIG. 3C is a lateral cross-sectional view of the ocular implant of FIG. 3A taken along section line C-C. Section line C-C intersects a spine of the ocular implant at the point where the width of the spine is at a minimum. A circumferential extent of the spine illustrated using dimension lines in FIG. 3C. With reference to FIG. 3C and FIG. 3B, it will be appreciated that the circumferential extent of frame is greater than the circumferential extent of the spine.

FIG. 4 is an isometric view showing a portion of the ocular implant shown in the previous figure. With reference to FIG. 4, it will be appreciated that the outer surfaces of the first spine, the second spine, the first strut, and the second strut define a generally cylindrical volume V. The shape of the ocular implant may be described using the cylindrical coordinates shown in FIG. 4.

In FIG. 5, a number of section lines are shown crossing the first strut and the second strut of the ocular implant. In the embodiment of FIG. 5, each strut undulates in a circumferential direction while, at the same time, extending in axial direction Z between the first spine and the second spine. The circumferential undulation of the first strut is illustrated in FIG. 6 using lateral cross-sectional drawings labeled with cylindrical coordinates.

FIG. 7 shows a plurality of cylindrical coordinate values corresponding with the cross-sectional views shown in the previous figure.

DETAILED DESCRIPTION

The following detailed description should be read with reference to the drawings, in which like elements in different drawings are numbered identically. The drawings, which are not necessarily to scale, depict exemplary embodiments and are not intended to limit the scope of the invention. Examples of constructions, materials, dimensions, and manufacturing processes are provided for selected elements. All other elements employ that which is known to those of skill in the field of the invention. Those skilled in the art will recognize that many of the examples provided have suitable alternatives that can be utilized.

Figure 1:
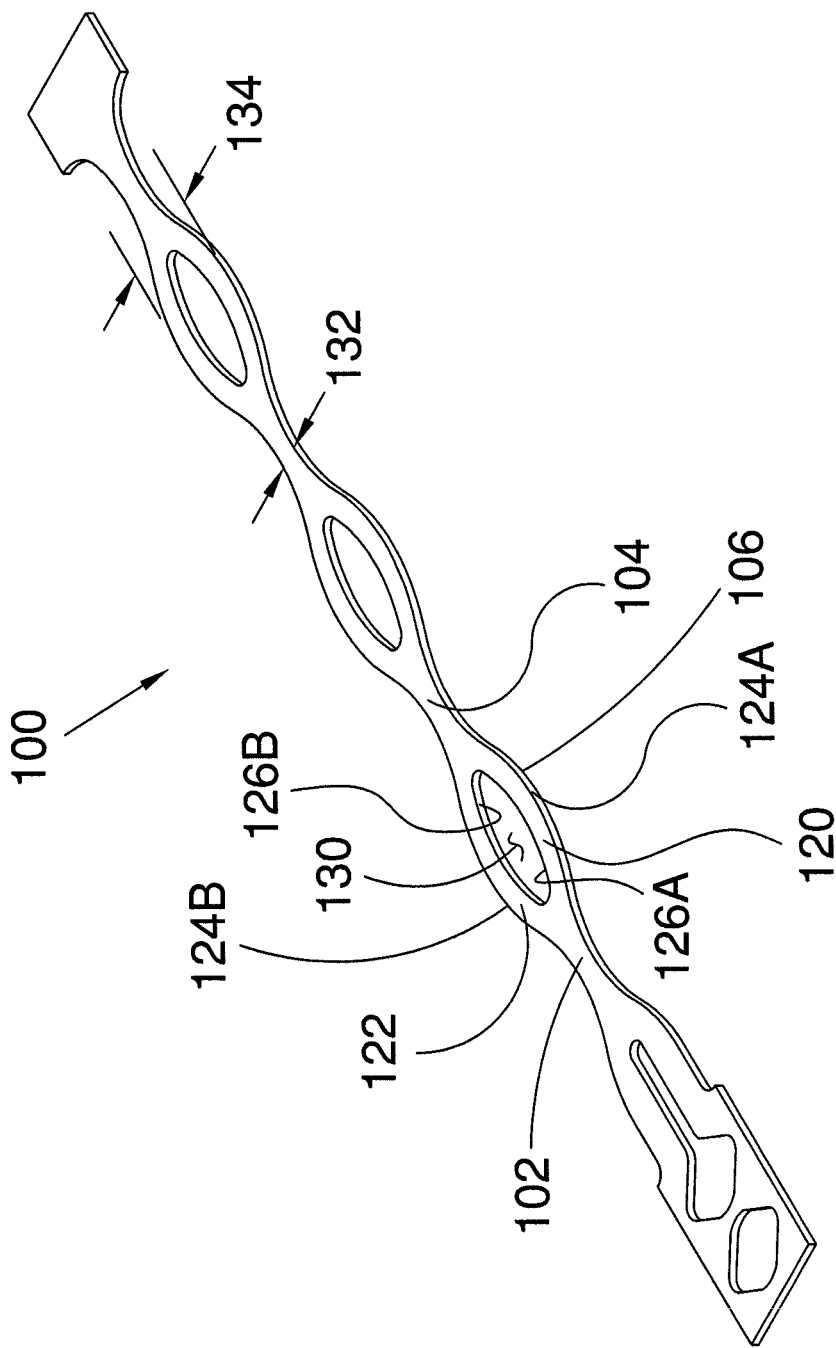
FIG. 1 is an isometric view showing a body that may be used to form an ocular implant in accordance with one exemplary embodiment of the invention. The body comprises a first spine, a second spine, and a first frame disposed between the first spine and the second spine. The first frame comprises a first strut and a second strut.

FIG. 1 is an isometric view showing a body 100 that may be used to form an ocular implant in accordance with one exemplary embodiment of the invention. Body 100 comprises a first spine 102, a second spine 104, and a first frame 106 disposed between first spine 102 and second spine 104. In the embodiment of FIG. 1, first frame 106 comprises a first strut 120 and a second strut 122. With reference to FIG. 1, it will be appreciated that each strut extends between first spine 102 and second spine 104.

First strut 120 of first frame 106 comprises a first edge 124A and a second edge 126A. With reference to FIG. 1, it will be appreciated that second strut 122 has a shape that is a mirror image of the shape of first strut 120. Second strut 122 comprises a first edge 124B and a second edge 126B. Second edge 126B of second strut 122 and second edge 126A of first strut 120 define a second opening 130. Second opening 130 generally divides first frame 106 into first strut 120 and second strut 122.

With continuing reference to FIG. 1, it will be appreciated that body 100 comprises a plurality of spines and a plurality of frames. In the embodiment of FIG. 1, these spines and frames are arranged in an ABAB pattern. Each spine has a first lateral extent 132 and each frame has a second lateral extent 134. With reference to FIG. 1, it will be appreciated that second lateral extent 134 is greater than first lateral extent 132.

Figure 2:
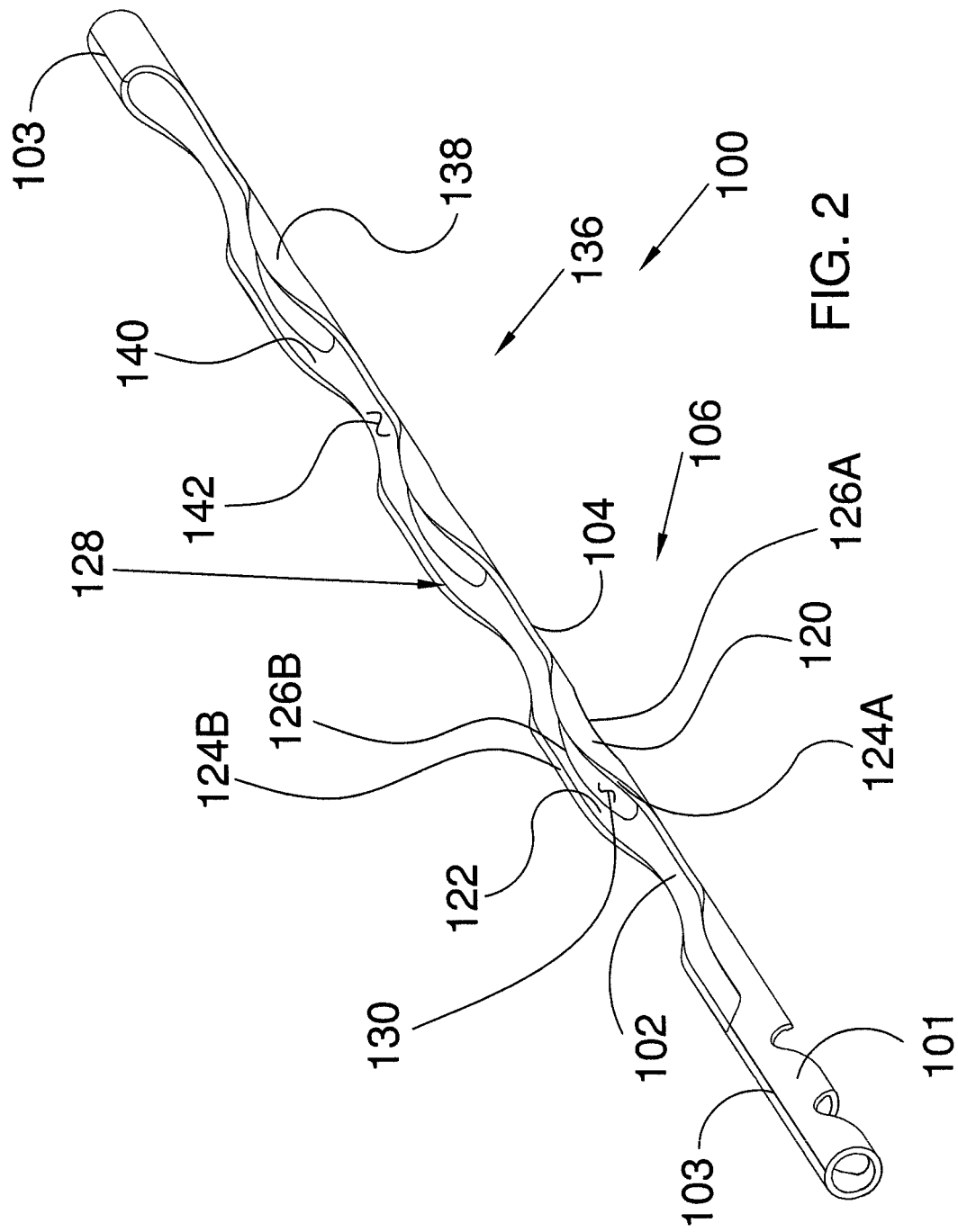
FIG. 2 is an isometric view of the body shown in the previous figure. In the embodiment of FIG. 2, the body is shaped to form an ocular implant having an outer surface defining a generally cylindrical volume. An inner surface of the body defines an elongate channel. The ocular implant may be inserted into Schlemm's canal of a human eye to facilitate the flow of aqueous humor out of the anterior chamber.

FIG. 2 is an isometric view of body 100 shown in the previous figure. In the embodiment of FIG. 2, body 100 is shaped to form an ocular implant 136 having an outer surface 138 defining a generally cylindrical volume. An inner surface 140 of body 100 defines an elongate channel 142. Ocular implant 136 may be inserted into Schlemm's canal of a human eye to facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 136 will support trabecular mesh tissue and Schlemm's canal tissue and will provide for improved communication between the anterior chamber and Schlemm's canal (via the trabecular meshwork) and between pockets or compartments along Schlemm's canal.

Elongate channel 142 of ocular implant 136 fluidly communicates with a first opening 128 as well as inlet portion 101. Various fabrication techniques may be used to fabricate ocular implant 136. For example, ocular implant 136 can be fabricated by providing a generally flat sheet of material and laser cutting the sheet of material to form body 100 shown in FIG. 1. The body 100 may then be formed into a generally tubular shape as shown in FIG. 2. Any adjoining edges (such as edges 103) may be, optionally, welded. By way of a second example, ocular implant 136 may be fabricated by providing a tube and laser cutting openings in the tube to form the shape shown in FIG. 2.

As shown in FIG. 2, ocular implant 136 comprises a first spine 102 and a second spine 104. A first frame 106 of ocular implant 136 is disposed between first spine 102 and second spine 104. In the embodiment of FIG. 2, first frame 106 comprises a first strut 120 that extends between first spine 102 and second spine 104. First frame 106 also comprises a second strut 122. Second strut 122 also extends between first spine 102 and second spine 104

First strut 120 of first frame 106 comprises a first edge 124A and a second edge 126A. As shown in FIG. 1, first edge 124A has a convex surface, and second edge 126A has a concave surface. Second strut 122 has a shape that is a mirror image of the shape of first strut 120. In FIG. 2, first opening 128 of ocular implant 136 can be seen extending between first edge 124A of first strut 120 and a first edge 124B of second strut 122. A second edge 126B of second strut 122 and second edge 126A of first strut 120 define a second opening 130. Second opening 130 and additional openings (e.g., first opening 128) defined by ocular implant 136 allow aqueous humor to flow laterally across and/or laterally through ocular implant 136. As shown in FIG. 2, openings 128 and 130 are shorter than the opening of elongate channel 142 extending along one side of implant 136.

Ocular implant 136 can be fabricated from various biocompatible materials possessing the necessary structural and mechanical attributes. Both metallic and non-metallic materials may be suitable. Examples of metallic materials include stainless steel, tantalum, gold, titanium, and nickel-titanium alloys known in the art as Nitinol. Nitinol is commercially available from Memry Technologies (Brookfield, Conn.), TiNi Alloy Company (San Leandro, Calif.), and Shape Memory Applications (Sunnyvale, Calif.).

Ocular implant 136 may include one or more therapeutic agents. One or more therapeutic agents may, for example, be incorporated into a polymeric coating that is deposited onto the outer surfaces of the struts and spines of the ocular implant. The therapeutic agent may comprise, for example, an anti-glaucoma drug. Examples of anti-glaucoma drugs include prostaglandin analogs. Examples of prostaglandin analogs include latanprost.

FIG. 3A is a plan view showing a portion of ocular implant 136 shown in the previous figure. Body 100 of ocular implant 136 comprises a first spine 102, a second spine 104, and a first frame 106 disposed between first spine 102 and second spine 104. In the embodiment of FIG. 3A, first frame 106 comprises a first strut 120 and a second strut 122. As shown, each strut undulates in a circumferential direction while, at the same time, extending in the axial direction Z between first spine 102 and second spine 104.

FIG. 3B is a lateral cross-sectional view of ocular implant 136 taken along section line B-B. Section line B-B intersects first strut 120 and second strut 122 at the point where the circumferential undulation of these struts is at its maximum. First strut 120 and second strut 122 form first frame 106. First frame 106 has a first circumferential extent 144 in the embodiment of FIG. 3B.

FIG. 3C is a lateral cross-sectional view of ocular implant 136 taken along section line C-C. Section line C-C intersects first spine 102 at the point where the width of first spine 102 is at a minimum. At this point, first spine 102 has a second circumferential extent 146. Second circumferential extent 146 of first spine 102 is illustrated using dimension lines in FIG. 3C. With reference to FIG. 3C and FIG. 3B, it will be appreciated that first circumferential extent 144 of first frame 106 is greater than second circumferential extent 146 of first spine 102.

FIG. 4 is an isometric view showing a portion of ocular implant 136 shown in the previous figure. With reference to FIG. 4, it will be appreciated that the outer surfaces of first spine 102, second spine 104, first strut 120, and second strut 122 define a portion of a generally cylindrical volume V. The shape of ocular implant 136 may be described using the cylindrical coordinates shown in FIG. 4. These cylindrical coordinates include a radius r, an angle $\theta$ and an axial dimension Z. Cylindrical coordinates may be conceptualized as an extension of two dimensional polar coordinates to include a longitudinal or axial dimension Z. The two dimensions of a typical polar coordinate system are radius r and angle $\theta$. In the embodiment of FIG. 4, dimension Z extends along a longitudinal axis 148 of cylindrical volume V.

As shown in FIG. 4, first strut 120 extends in axial direction Z between first spine 102 and second spine 104. Second strut 122 also extends between first spine 102 and second spine 104. In the embodiment of FIG. 4, the radius r of the outer surface of each strut remains substantially constant. The angular dimension θ of a first edge 124A of first strut varies as first strut 120 extends in the axial direction Z between first spine 102 and second spine 104. Similarly, the angular dimension θ of a second edge 126A of second strut varies as second strut 122 extends in the axial direction Z between first spine 102 and second spine 104.

Figure 5:
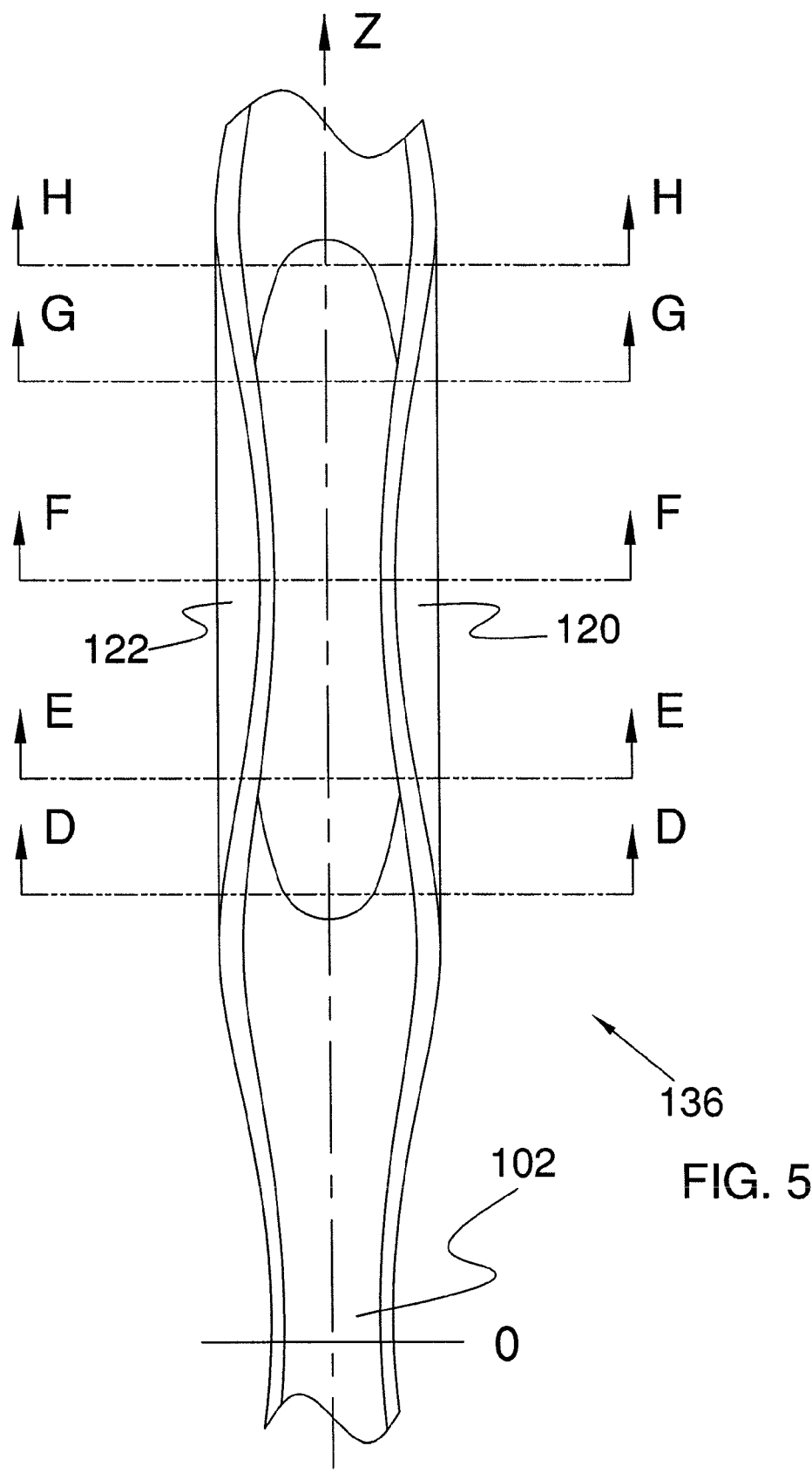
FIG. 5 is an enlarged plan view showing a portion of the ocular implant shown in the previous figure.
Figure 6E:
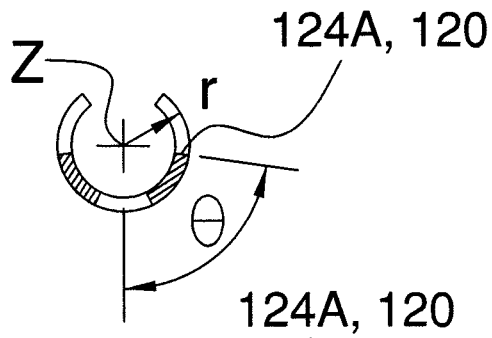
FIG. 6A through 6E are lateral cross-sectional views of the ocular implant shown in the previous figure. These cross-sectional views correspond to the section lines shown in the previous figure. With reference to these cross-sectional views, it will be appreciated that the angular dimension θ associated with a first edge of the first strut undulates as the first strut extends in an axial direction Z between the first spine and the second spine. In the embodiment of FIG. 6, the radius r of the outer surface of the first strut remains substantially constant as the first strut extends in the axial direction Z between the first spine and the second spine.
Figure 6D:
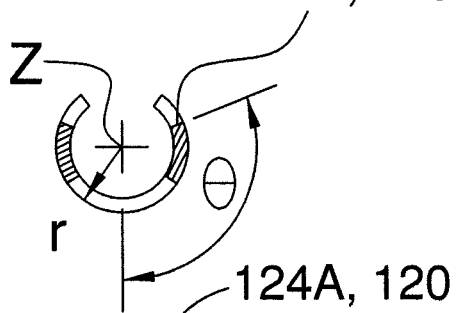
Figure 6C:
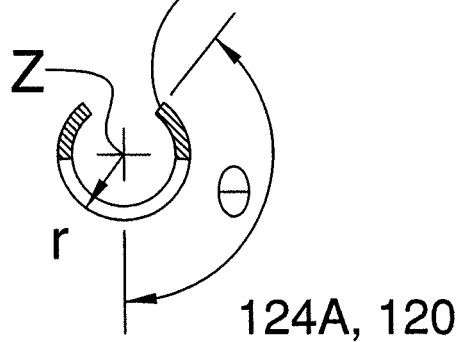
Figure 6B:
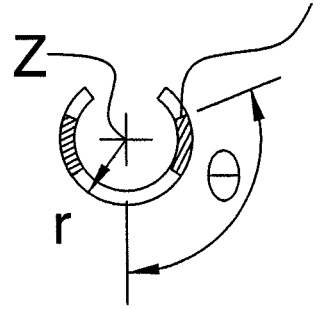
Figure 6A:
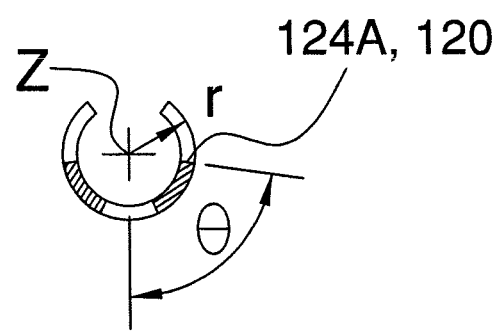

FIG. 5 is an enlarged plan view showing a portion of ocular implant 136 shown in the previous figure. In FIG. 5, a number of section lines are shown crossing first strut 120 and second strut 122 of ocular implant 136. In the embodiment of FIG. 5, each strut undulates in a circumferential direction while, at the same time, extending in axial direction Z between first spine 102 and second spine 104. The circumferential undulation of first strut 120 is illustrated in the next figure using lateral cross-sectional drawings labeled with cylindrical coordinates.

FIGS. 6A through 6E are lateral cross-sectional views of ocular implant 136 shown in the previous figure. These cross-sectional views correspond to the section lines shown in the previous figure. With reference to these cross-sectional views, it will be appreciated that the angular dimension θ associated with first edge 124A of first strut 120 undulates as first strut 120 extends in an axial direction Z between the first spine and the second spine. In the embodiment of FIG. 6, the radius r of the outer surface of first strut 120 remains substantially constant as first strut 120 extends in axial direction Z between the first spine and the second spine.

FIG. 7 shows a plurality of cylindrical coordinate values corresponding with the cross-sectional views shown in the previous figure. With reference to the numerical values shown in FIG. 7, it will be appreciated that the numerical value of angular dimension θ of first edge 124 first increases, then decreases, as first strut 120 extends in an axial direction Z between the first spine and the second spine. The numerical value r remains constant as first strut 120 extends in axial direction Z between the first spine and the second spine.

Figure 8:
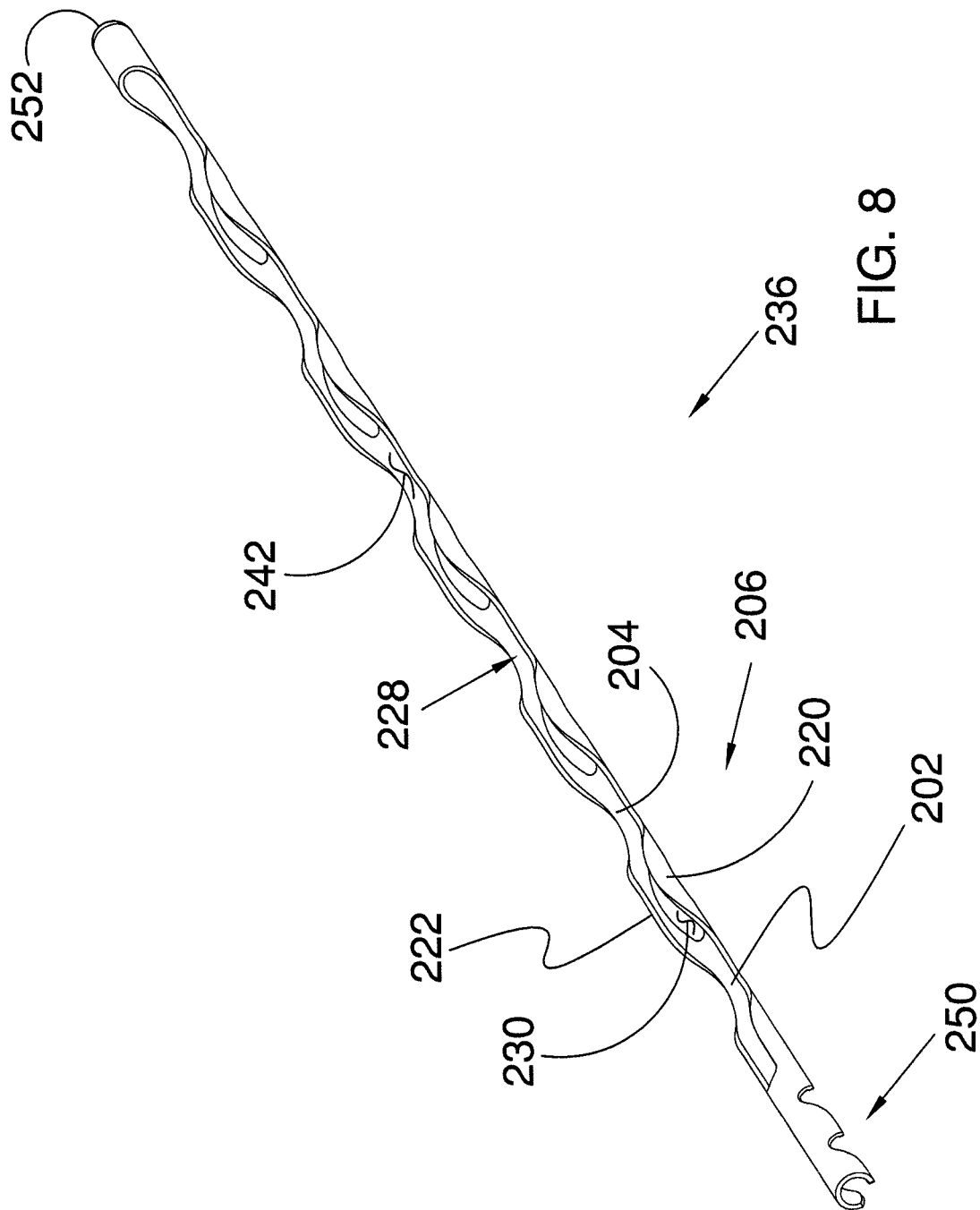
FIG. 8 is an isometric view of an ocular implant in accordance with an additional exemplary embodiment of the invention.

FIG. 8 is an isometric view of an ocular implant 236 in accordance with an additional exemplary embodiment of the invention. As shown in FIG. 8, ocular implant 236 comprises a first spine 202 and a second spine 204. A first frame 206 of ocular implant 236 is disposed between first spine 202 and second spine 204. In the embodiment of FIG. 8, first frame 206 comprises a first strut 220 that extends between first spine 202 and second spine 204. First frame 206 also comprises a second strut 222. With reference to FIG. 8, it will be appreciated that second strut 222 also extends between first spine 202 and second spine 204.

Ocular implant 236 of FIG. 8 defines a channel 242 that opens into a first opening 228. In FIG. 8, first opening 228 of ocular implant 236 can be seen extending between first strut 220 and second strut 222. First strut 220 and second strut 222 also define a second opening 230. First opening 228, second opening 230, and the additional openings shown in FIG. 8, allow aqueous humor to flow laterally across and/or laterally through ocular implant 236.

In the embodiment of FIG. 8, an inlet portion 250 is formed near a proximal end of ocular implant 236. Inlet portion 250 may extend through the trabecular meshwork into the anterior chamber of the eye when a portion of the ocular implant lies in Schlemm's canal.

In the embodiment of FIG. 8, a blunt tip 252 is disposed at a distal end of ocular implant 236. In some useful embodiments of ocular implant 236, blunt tip 252 has a generally rounded shape. In the embodiment shown in FIG. 8, blunt tip 252 has a generally hemispherical shape. The generally rounded shape of blunt tip 252 may increase the likelihood that body 200 will track Schlemm's canal as ocular implant 236 is advanced into the canal during an implant procedure.

In FIG. 8, ocular implant 236 is pictured assuming a generally straight shape. Embodiments of ocular implant 236 are possible which have a generally curved resting shape. Ocular implant 236 may be fabricated, for example, by laser cutting a tube to create the shape shown in FIG. 8. When this is the case, it may be desirable to rotate a straight tubular workpiece during the laser cutting process. After the laser cutting process, the ocular implant can be heat-set so that the ocular implant is biased to assume a selected shape (e.g., a generally curved shape).

Figure 9:
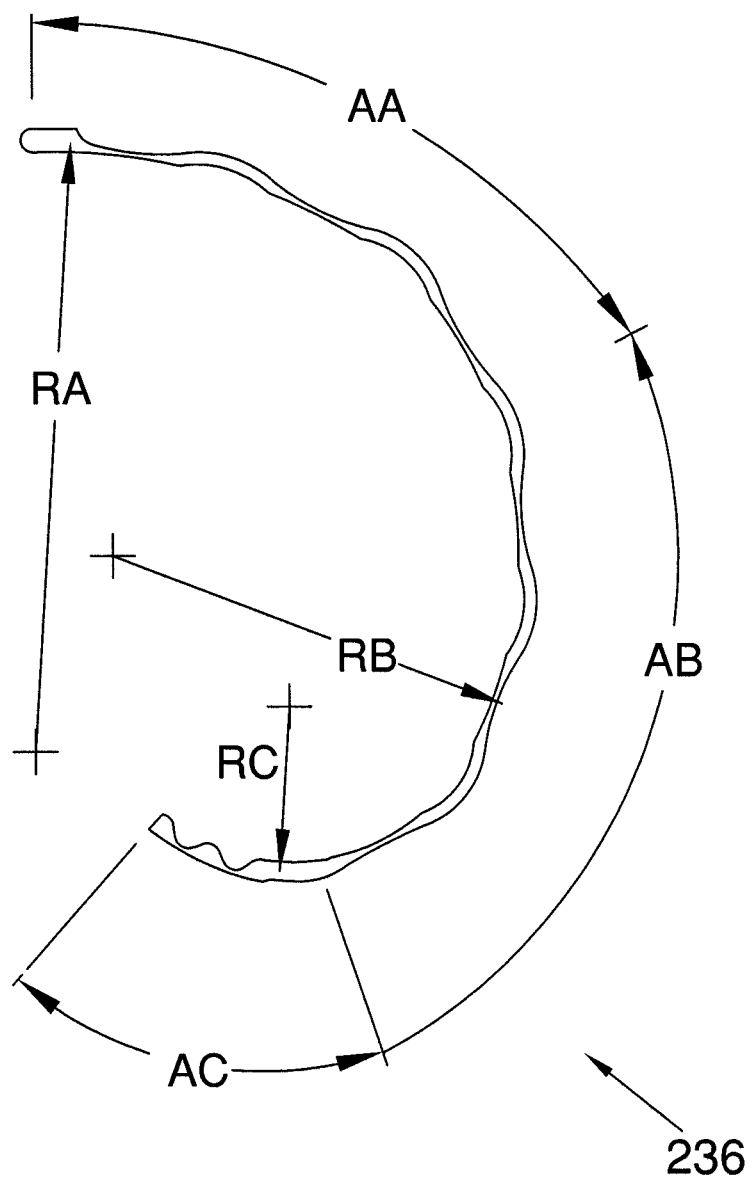
FIG. 9 is a plan view of the ocular implant shown in the previous figure. In the embodiment of FIG. 9, the ocular implant has an at rest shape that is generally curved.

FIG. 9 is a plan view of ocular implant 236 shown in the previous figure. In the embodiment of FIG. 9, ocular implant 236 has an at rest shape that is generally curved. This at rest shape can be established, for example, using a heat-setting process. The ocular implant shape shown in FIG. 9 includes a distal radius RA, a proximal radius RC, and an intermediate radius RB. In the embodiment of FIG. 9, distal radius RA is larger than both intermediate radius RB and proximal radius RC. Also in the embodiment of FIG. 9, intermediate radius RB is larger than proximal radius RC and smaller than distal radius RA. In one useful embodiment, distal radius RA is about 0.310 inches, intermediate radius RB is about 0.215 inches and proximal radius RC is about 0.105 inches.

In the embodiment of FIG. 9, a distal portion of the ocular implant follows distal radius RA along an arc extending across an angle AA. A proximal portion of the ocular implant follows proximal radius RC along an arc extending across an angle AC. An intermediate portion of the ocular implant is disposed between the proximal portion and the distal portion. The intermediate portion follows radius RB and extends across an angle AB. In one useful embodiment, angle AA is about 55 degrees, angle AB is about 79 degrees and angle AC is about 60 degrees.

Ocular implant 236 may be used in conjunction with a method of treating a patient. Some such methods may include the step of inserting a core member into a lumen defined by ocular implant 236. The core member may comprise, for example, a wire or tube. The distal end of the ocular implant may be inserted into Schlemm's canal. The ocular implant and the core member may then be advanced into Schlemm's canal until the ocular implant has reached a desired position. The core member may then be withdrawn from the ocular implant.

Figure 10:
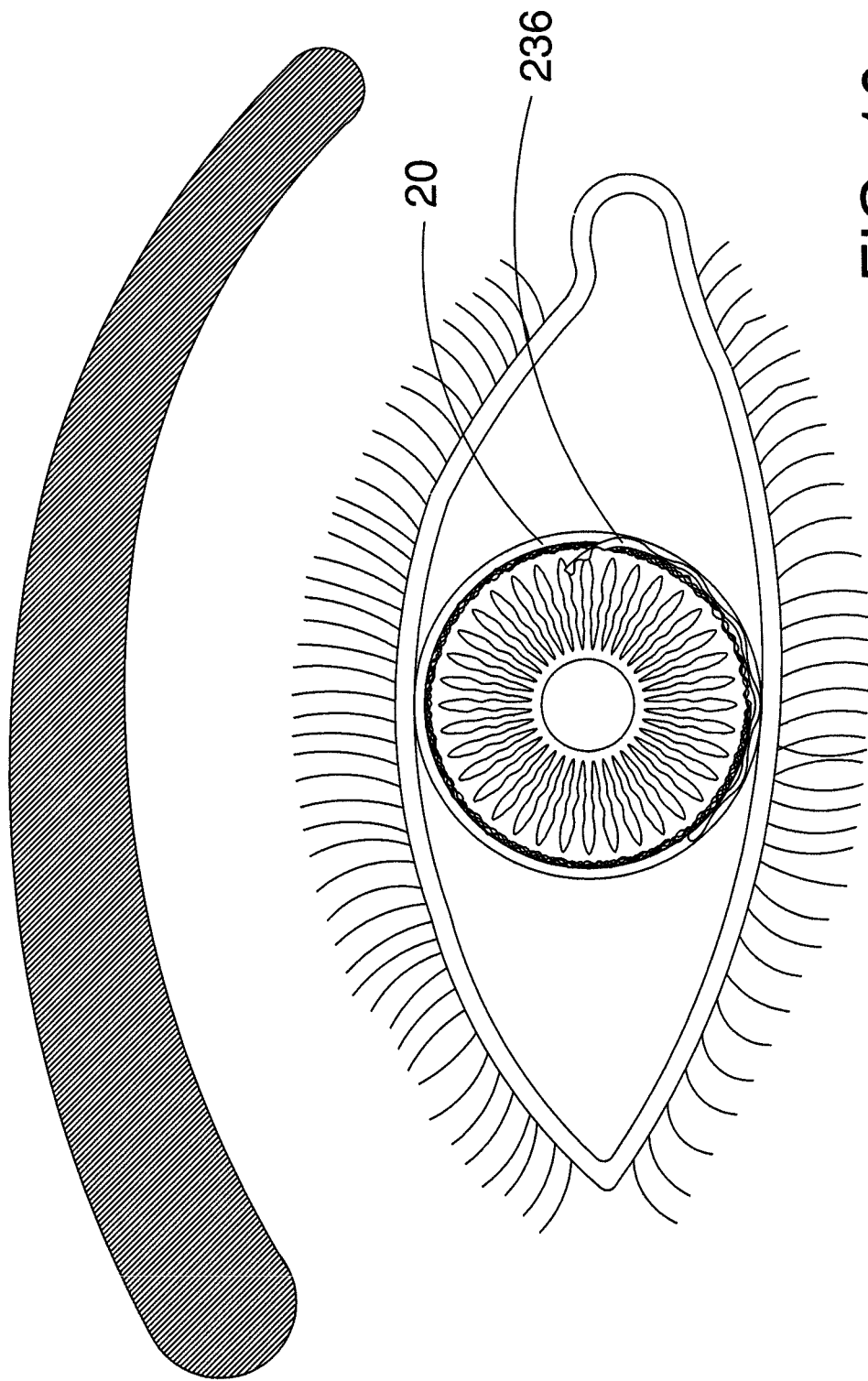
FIG. 10 shows the ocular implant of the previous figure in place within a human eye.

FIG. 10 shows ocular implant 236 of the previous figure in place within a human eye. The eye of FIG. 10 includes an anterior chamber that is covered by a cornea. The iris of the eye is visible through the cornea and the anterior chamber. The anterior chamber is filled with aqueous humor which helps maintain the generally hemispherical shape of the cornea.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens)

that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

The structures that drain aqueous humor from the anterior chamber include Schlemm's canal and a large number of veins that communicate with Schlemm's canal via a plurality of outlets. In FIG. 10, Schlemm's canal 20 can be seen encircling the iris of the eye. Ocular implant 236 may be inserted into Schlemm's canal 20 to facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 236 will support trabecular mesh tissue and Schlemm's canal tissue and will provide for improved communication between the anterior chamber and Schlemm's canal (via the trabecular meshwork) and between pockets or compartments along Schlemm's canal.

Figure 11:
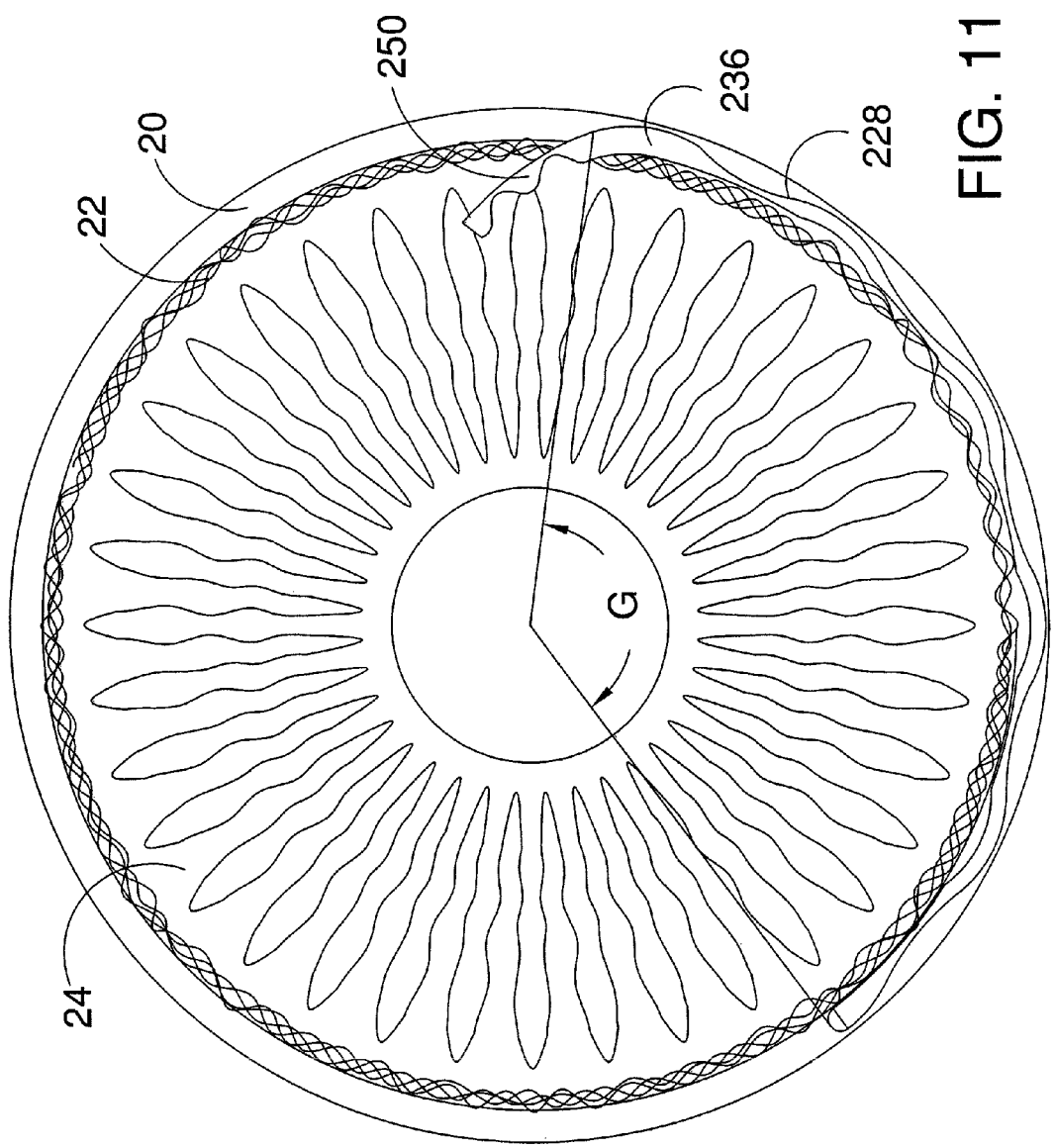
FIG. 11 is an enlarged plan view showing a portion of the eye shown in the previous figure.

FIG. 11 is an enlarged plan view showing a portion of the eye shown in the previous figure. With reference to FIG. 11, it will be appreciated that ocular implant 236 extends through Schlemm's canal 20 across an angle G. Various implant sizes are possible, and different implant sizes may span a different angle G when placed in Schlemm's canal. Examples of angular spans that may be suitable in some applications include 60°, 90°, 150° and 180°.

In FIG. 11, an inlet portion 250 of ocular implant 236 is shown extending through trabecular mesh 22. Aqueous humor may exit anterior chamber 24 and enter Schlemm's canal 20 by flowing through inlet portion 250 of ocular implant 236. Aqueous humor may also exit anterior chamber 24 and enter Schlemm's canal 20 by flowing through the trabecular mesh 22 of the eye. With reference to FIG. 11, it will be appreciated that the spines of ocular implant 236 support trabecular mesh 22.

Aqueous humor exits Schlemm's canal 20 by flowing through a number of outlets. After leaving Schlemm's canal 20, aqueous humor travels through a network passages and veins and is absorbed into the blood stream. Schlemm's canal typically has a non-circular cross-sectional shape whose diameter can vary along the canal's length and according to the angle at which the diameter is measured. In addition, there may be multiple partial pockets or partial compartments (not shown in these figures) formed along the length of Schlemm's canal. The shape and diameter of portions of Schlemm's canal and the existence and relative location of partial pockets or compartments may limit or prevent fluid flow from one point of Schlemm's canal to another. Hence, each outlet from Schlemm's canal may drain only a portion of Schlemm's canal. This condition may be improved by placing ocular implant 236 in Schlemm's canal. Ocular implant 236 shown in FIG. 11 includes a plurality of struts, spines and openings. When in place within the eye, ocular implant 236 will support trabecular mesh tissue and Schlemm's canal tissue and will provide for improved communication between the anterior chamber and Schlemm's canal and between pockets or compartments along Schlemm's canal.

In FIG. 11, first opening 228 of ocular implant 236 is shown facing radially outward in Schlemm's canal 20. Aqueous humor can exit Schlemm's canal 20 by flowing through outlets that radiate away from and communicate with Schlemm's canal 20. After flowing through these outlets, this excess aqueous humor can enter the venous bloodstream be carried out of the eye by venous blood flow. The diameter of ocular implant 236 can range from 0.005 inches to 0.04 inches, preferably from 0.005 inches to 0.02 inches, in order to lie within and support Schlemm's canal.

While exemplary embodiments of the present invention have been shown and described, modifications may be made, and it is therefore intended in the appended claims to cover all such changes and modifications which fall within the true spirit and scope of the invention.

What is claimed is:

1. An ocular implant comprising:
   a longitudinally extending body having an inlet portion and a Schlemm's canal portion distal to the inlet portion, the inlet portion, when in use, extending into and in fluid communication with an anterior chamber of a human eye;
   a plurality of alternating spines and frames positioned longitudinally along at least a portion of the Schlemm's canal portion wherein the plurality of alternating spines and frames define a central channel extending therethrough with the central channel in fluid communication with the inlet portion;
   each of the spines having edges partially defining an opening in fluid communication with the central channel;
   each of the frames including first and second struts, the first and second struts each having an edge contiguous with an edge of an adjacent spine, the edges defining the opening in fluid communication with the central channel, the frames each having a circumferential extent around the central channel greater than a circumferential extent of an adjacent spine.

2. The ocular implant of claim 1, wherein an angular dimension of the edges of the first and second struts varies longitudinally along each strut.

3. The ocular implant of claim 2, wherein each frame includes a proximal portion, a central portion and a distal portion with the central portion having a circumferential extent greater than the circumferential extent of the proximal and distal portions.

4. The ocular implant of claim 1 wherein the Schlemm's canal portion is curved, the opening defined by the edges of the spines and struts being disposed on the outside of the curve.

5. The ocular implant of claim 4 wherein the spines are disposed on the inside of the curve.

6. The ocular implant of claim 1 wherein the longitudinally extending body has a length sufficient to extend the ocular implant in Schlemm's canal at least about 60° around the pupil of the eye.

7. The ocular implant of claim 1 wherein circumferential material coverage in any cross section perpendicular to a longitudinal axis of the ocular implant is less than 360° over the Schlemm's canal portion of the implant.

8. An ocular implant comprising:
   a longitudinally extending body having an inlet portion and a Schlemm's canal portion distal to the inlet portion, the inlet portion, when in use, extending into and in fluid communication with an anterior chamber of a human eye and a central channel defined by the Schlemm's canal portion;
   a first spine extending longitudinally along the Schlemm's canal portion and having edges partially defining a first opening in fluid communication with the central channel;

a second spine extending longitudinally along the Schlemm's canal portion and having edges partially defining the first opening, the second spine being disposed distal to the first spine;

a first frame extending longitudinally along the Schlemm's canal portion and disposed between the first and second spine, the first frame including first and second struts, the first and second struts each having a first edge partially defining the first opening, the first frame having a circumferential extent around the central channel greater than a circumferential extent of the first spine and a circumferential extent of the second spine; and, a second frame extending longitudinally along the Schlemm's canal portion, the second frame being disposed distal to the second spine, the second frame comprising first and second struts, the second frame's first and second struts each having a first edge partially defining the first opening, the second frame having a circumferential extent around the central channel greater than the circumferential extent of the second spine.

9. The ocular implant of claim 8 wherein the first and second frames each includes a proximal portion, a central portion and a distal portion with the circumferential extent of at least one of the frames being greater in the central portion than the proximal and distal portions.

10. The ocular implant of claim 8 wherein the Schlemm's canal portion is curved, the first opening being disposed on the outside of the curve.

11. The ocular implant of claim 10 wherein the spines are disposed on the inside of the curve.

12. The ocular implant of claim 8 wherein the longitudinally extending body has a length sufficient to extend the ocular implant in Schlemm's canal at least about 60° around the pupil of the eye.

13. An ocular implant comprising:

an inlet portion and a Schlemm's canal portion distal to the inlet portion, the inlet portion being disposed at a proximal portion of the implant and configured to be placed within an anterior chamber of a human eye, the inlet portion having an inlet adapted to be in fluid communication with the anterior chamber;

the Schlemm's canal portion having a diameter between 0.005 inches and 0.04 inches with a central channel in fluid communication with the inlet;

the Schlemm's canal portion further having a first spine extending longitudinally along the central channel and having edges partially defining a first opening in fluid communication with the central channel and a second spine extending longitudinally along the central channel and having edges partially defining the first opening, the second spine being disposed distal to the first spine with a first frame extending longitudinally along the central channel, the first frame being disposed distal to the first spine and proximal to the second spine, the first frame comprising first and second struts, the first and second struts each having a first edge partially defining the first opening, the first frame having a circumferential extent around the central channel greater than a circumferential extent of the first spine and a circumferential extent of the second spine, the circumferential extent of the first frame being less at a distal portion of the first frame than at a central portion of the first frame;

the Schlemm's canal portion also including a second frame extending longitudinally along the central channel, the second frame being disposed distal to the second spine, the second frame comprising first and second struts, the second frame's first and second struts each having a first edge partially defining the first opening, the second frame having a circumferential extent around the central channel greater than the circumferential extent of the first spine and the circumferential extent of the second spine, the circumferential extent of the second frame being less at a distal portion of the second frame than at a central portion of the second frame.

14. The ocular implant of claim 13 wherein the circumferential extent of each of the first and second frames is less at a proximal portion of the frame than at the central portion of the frame.

15. The ocular implant of claim 13 wherein the first frame's first and second struts each further comprises a second edge defining a second opening in fluid communication with the central channel, and the second frame's first and second struts each further comprises a second edge defining a third opening in fluid communication with the central channel.

16. The ocular implant of claim 13 wherein the Schlemm's canal portion is curved, the first opening being disposed on the outside of the curve.

17. The ocular implant of claim 16 wherein the spines are disposed on the inside of the curve.

18. The ocular implant of claim 13 wherein the Schlemm's canal portion has a length sufficient to extend the ocular implant in Schlemm's canal at least about 60° around the pupil of the eye.

19. The ocular implant of claim 13 wherein circumferential material coverage in cross sections perpendicular to a longitudinal axis of the ocular implant is less than 360° over an entire length of the implant.

\* \* \* \* \*